United States Patent [19]

Bonaldi et al.

[11] 4,379,093

[45] Apr. 5, 1983

[54] PROCESS FOR PREPARING HIGH PURITY URSODEOXYCHOLIC ACID

[75] Inventors: Antonio Bonaldi, Chiuduno; Egidio Molinari, Longone al Segrino, both of Italy

[73] Assignee: Erregierre S.p.A., Bergamo, Italy

[21] Appl. No.: 277,005

[22] Filed: Jun. 24, 1981

[30] Foreign Application Priority Data

Apr. 14, 1981 [IT] Italy ............................... 21137 A/81

[51] Int. Cl.$^3$ .............................................. C07J 9/00
[52] U.S. Cl. .................................................. 260/397.1
[58] Field of Search ...................................... 260/397.1

[56] References Cited

U.S. PATENT DOCUMENTS 4,277,408  7/1981  Pavan et al. .................... 260/397.1

FOREIGN PATENT DOCUMENTS 24292    3/1981  European Pat. Off. ......... 260/397.1
2036749  7/1980  United Kingdom ............. 260/397.1

OTHER PUBLICATIONS

Chemical Abstracts, vol. 82 (1975), Par. 125,527(b).
Acta Chemica Scandinavica, vol. 14, No. 1, 1960, Copenhagen (DK) B. Samuelsson: pp. 17–20, "Preparation of Ursodeoxycholic Acid and 3a, 7β, 12a–Trihydroxycholanic Acid".

Chemical Abstracts, vol. 51, No. 22, Nov. 25, 1957, col. 17965b–e, Columbus, Ohio (US).
Chemical Abstracts, vol. 82, No. 19, May 12, 1975, p. 576, Abstract No. 125527b, Columbus, Ohio (US).
Chemical Abstracts, vol. 81, No. 19, Nov. 11, 1974, p. 565, Abstract No. 120870c, Columbus, Ohio (US).

Primary Examiner—Elbert L. Roberts
Attorney, Agent, or Firm—Stevens, Davis, Miller & Mosher

[57] ABSTRACT

A process for preparing very pure ursodeoxycholic acid starting from cholic acid (I) by:
(a) selectively oxidizing it to 3 alpha, 12 alpha-dihydroxy-7-ketocholanic acid (II)
(b) reducing acid (II) to 3 alpha, 7 beta, 12 alpha-trihydroxy-cholanic acid (III)
(c) oxidizing a 3,7-ester of acid (III) to 3 alpha, 7 beta-dihydroxy-12-keto-5-beta-cholanic acid (IV) by treatment with hypochlorite followed by hydrolysis
(d) preparing the tris-trimethylsilyl derivative of acid (IV)
(e) eliminating the trimethylsilyl groups
(f) reducing the very pure acid (IV) by the Wolff-Kishner method to ursodeoxycholic acid.
Alternatively, the Wolff-Kishner method can be applied directly to the tris-trimethylsilyl derivative, and the trimethylsilyl groups can be eliminated from the final product.

4 Claims, No Drawings

PROCESS FOR PREPARING HIGH PURITY URSODEOXYCHOLIC ACID

This invention relates to a new industrial process for producing ursodeoxycholic acid (3 alpha-7 beta-dihydroxycholanic acid) of high purity, and in particular not contaminated by the chenodeoxycholic acid epimer (3 alpha-7 beta-dihydroxycholanic acid).

Ursodeoxycholic acid is known as a product of considerable interest in human therapy, in which it is used for its multiple functions such as solubilising bile calculi, lowering the percentage of cholesterol in the blood, lowering glycaemia, as a diuretic, and as an accelerant for lipid metabolism.

The processes used at the present time for producing ursodeoxycholic acid all essentially fall within the same reaction scheme, which comprises as its essential stage the oxidation of chenodeoxycholic acid (A) to 3α-hydroxy-7-keto-cholanic acid (B), which is hydrogenated to ursodeoxycholic acid (C):

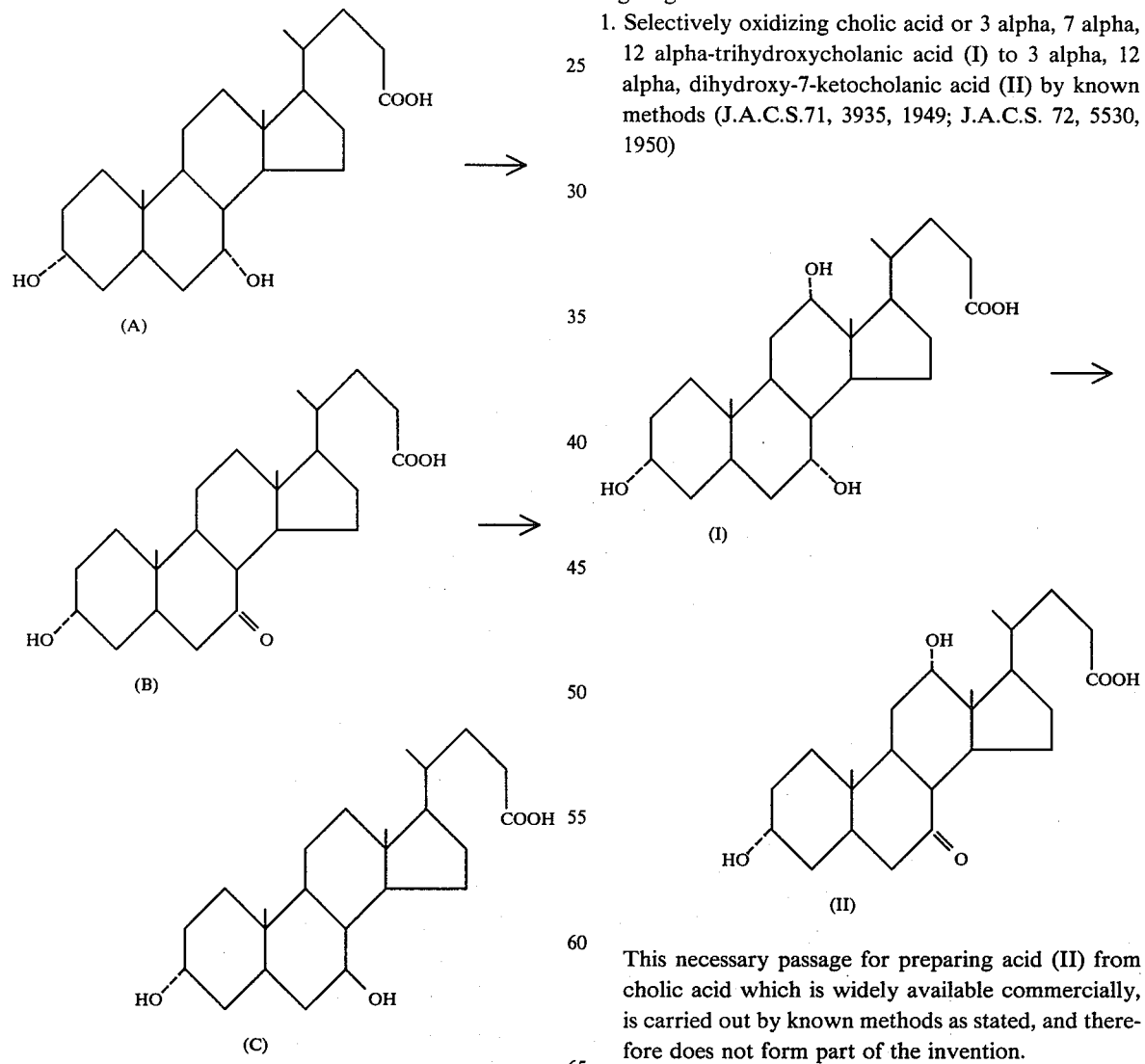

The drawback of known processes comprising said series of reactions lies in the fact that in all cases the reduction of compound B leads to a mixture of isomers consisting of about 80% of compound C and 20% of compound A or chenodeoxycholic acid, which is difficult to eliminate.

All the processes proposed up to the present time for separating the mixture of products A and C are industrially costly and of limited efficiency.

The object of the present invention is a new process which enables ursodeoxycholic acid to be prepared directly at pharmaceutical purity, and in particular free from chenodeoxycholic acid, without subsequent complicated and costly purification processes being necessary.

The new process uses cholic acid as its starting substance, but arrives at ursodeoxycholic acid by way of a completely new series of reactions which lead to the preparation of intermediate products which are also new. Essentially the new process comprises the following stages:

1. Selectively oxidizing cholic acid or 3 alpha, 7 alpha, 12 alpha-trihydroxycholanic acid (I) to 3 alpha, 12 alpha, dihydroxy-7-ketocholanic acid (II) by known methods (J.A.C.S.71, 3935, 1949; J.A.C.S. 72, 5530, 1950)

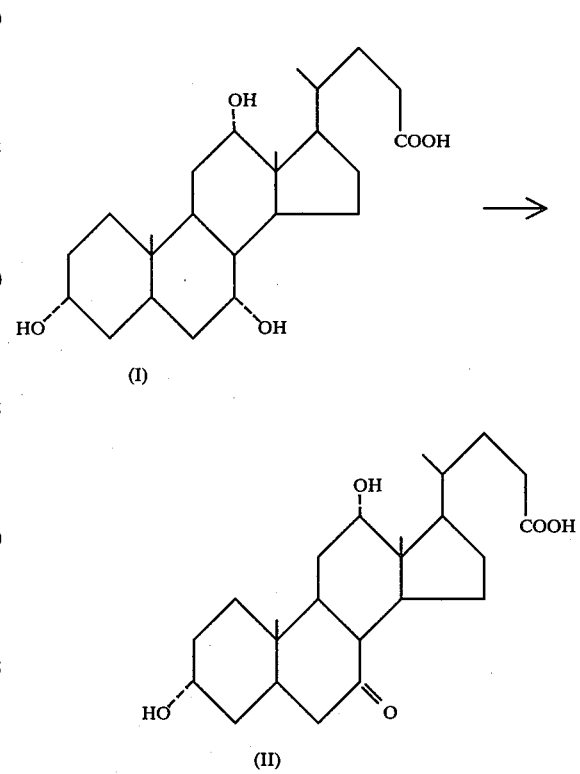

This necessary passage for preparing acid (II) from cholic acid which is widely available commercially, is carried out by known methods as stated, and therefore does not form part of the invention.

2. Reducing acid (II) to 3 alpha, 7 beta, 12 alpha-trihydroxy-cholanic acid (III) by treating its solution in a 1–4 C alcohol with alkaline metals

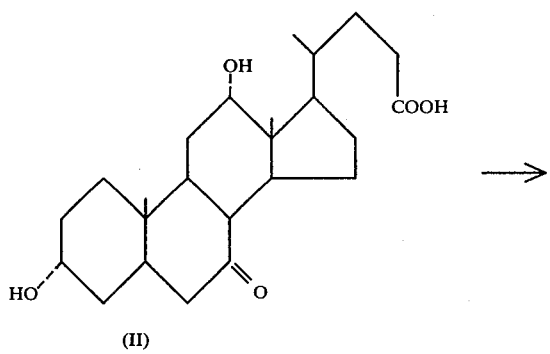

(II)

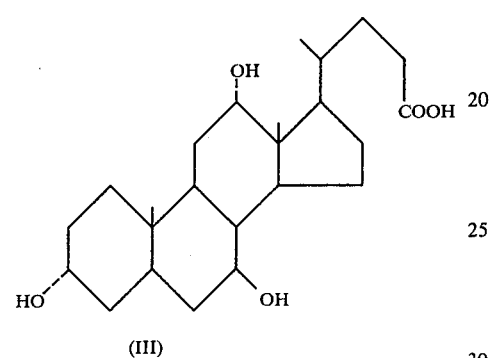

(III)

In reality, in this reaction, acid (III) forms together with a limited quantity, of between 10 and 15%, of the corresponding 7 alpha isomer or cholic acid (I).

3 alpha, 7 beta, 12 alpha-trihydroxycholanic acid (III) can be obtained in the pure state by crystallization from suitable solvents or by preparing products esterified completely or partly in positions 3, 7, 12 and 24, and purifying the esters obtained by crystallization from suitable solvents. Acid (III) is released from the pure ester thus obtained by alkaline saponification.

However, for the purposes of the present invention it is not necessary to obtain pure acid (III), and instead it can be used in the next stage in the state in which it is obtained, i.e. impure with cholic acid, provided it is suitably esterified in position 3 and 7 with acids, and possibly in position 24 with 1–4 C alcohol. These esterifications can, if required, be carried out in succession, by the normal esterification methods. The products of formula:

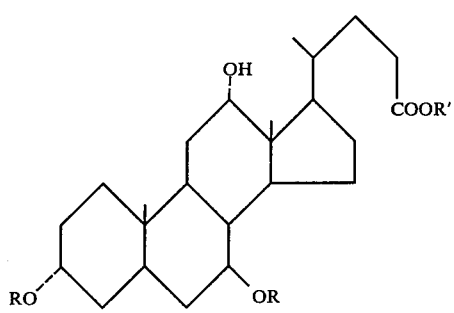

in which R=H or an acid radical preferably chosen from the group consisting of aliphatic acid radicals of 2–6 C atoms, simple or substituted benzoic acid, succinic acid or glutaric acid, and R'=H or an aliphatic radical containing 1–4 C atoms, are new compounds.

3. The 3 alpha, 7 beta, 12 alpha-trihydroxy-5 beta-cholanic acid (III) esterified in position 3 and 7 is oxidized to 3 alpha, 7 beta-dihydroxy-12 keto-5 beta-cholanic acid by means of alkaline hypochlorite in acetic acid in accordance with the equation:

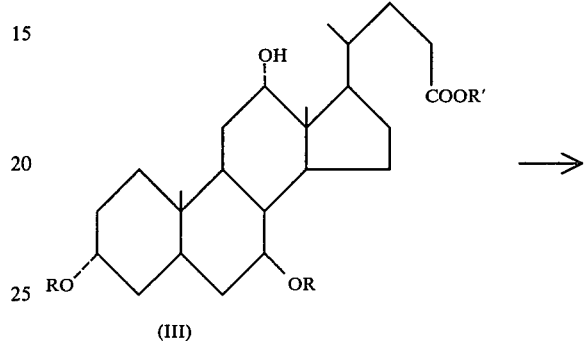

(III)

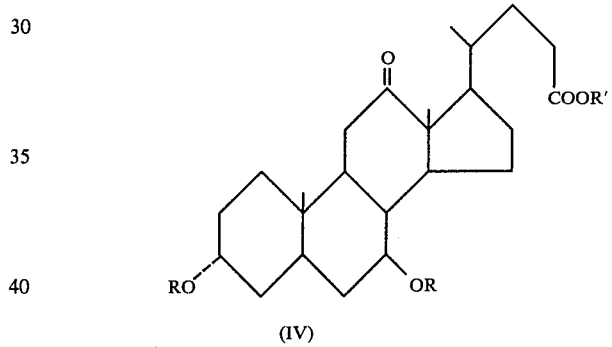

(IV)

in which R and R' are as stated heretofore. The excess hypochlorite is destroyed with bisulphite. Free 3 alpha, 7 beta-dihydroxy-12-keto-5-beta-cholanic acid is obtained by saponification with dilute strong alkali followed by acidification.

The free acid (IV) thus obtained contains impurities consisting mainly of 3 alpha, 7 alpha-dihydroxy-12-keto-5-beta-cholanic acid and unreacted 3 alpha, 7 beta, 12 alpha-trihydroxycholanic acid.

The products of formula (IV) are new compounds.

4. Purification of the 3 alpha, 7 beta-dihydroxy-12-keto-5 beta-cholanic acid by preparing its tris-trimethylsilyl derivative, by treating it in an organic solvent solution with a silanizing agent such as bis-trimethylsilylurea, hexamethyldisilazane, or bis-trimethylsilylacetamide at a temperature of between 30° and 100° C.:

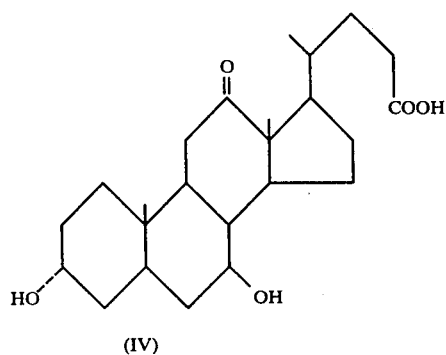

(IV)

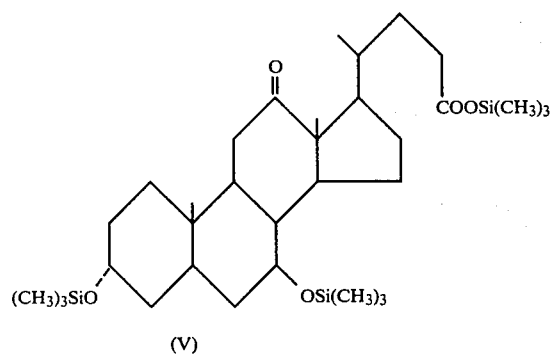

(V)

In this respect, it has been unexpectedly found that compound (V) has very poor solubility in organic solvents, whereas the tris-trimethylsilyl derivatives of the impurities, and in particular of 3 alpha, 7 alpha-dihydroxy-12-keto-5 beta-cholanic acid, are highly soluble in the same solvents.

The compounds of formula (V) are also new compounds.

5. Elimination of the trimethylsilyl groups by acid hydrolysis, preferably with HCl in aqueous solution or in an organic solvent in accordance with the equation:

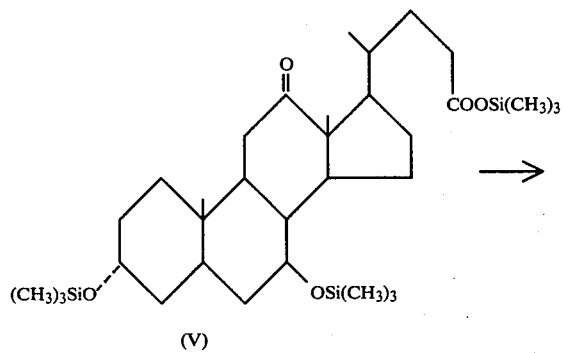

(V)

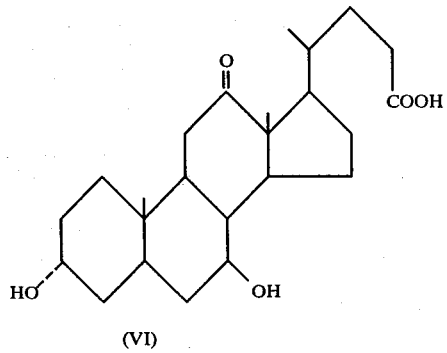

(VI)

6. Reduction of 3 alpha, 7 beta-dihydroxy-12-keto-5 beta-cholanic acid to ursodeoxycholic acid in accordance with the Wolff-Kisher method by heating to 200° C. with hydrazine hydrate in the presence of an alkaline base and triethylene glycol

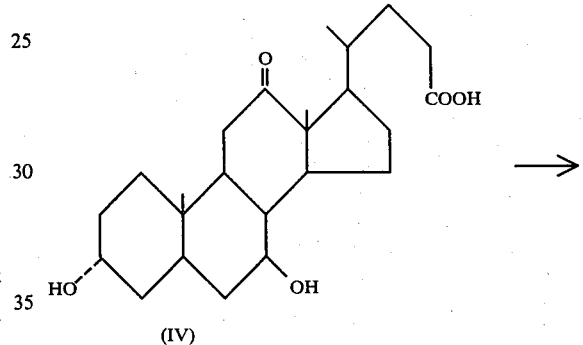

(IV)

(C)

Stages (5) and (6) can be reversed, in the sense that the Wolff-Kishner reduction can be carried out on the tris-trimethylsilane derivative, and the trimethylsilyl groups can be eliminated from the already reduced compound, i.e. from the tris-trimethylsilyl derivative of the high purity ursodeoxycholic acid.

The two processes alternatives give substantially equivalent results.

The new process according to the present invention has the advantage of using a widely available starting substance, and of converting it into ursodeoxycholic acid by a limited number of stages using reactions which can be carried out simply and with high selectivity.

It has the further advantage of leading directly to a product of pharmaceutical purity without requiring subsequent complicated and costly purification processes. Some embodiments are given hereinafter, in order to make the process according to the invention more easily reproducible, but these are in no case intended as limiting the scope of the invention.

EXAMPLE 1

100 grams of 3 alpha, 12 alpha-dihydroxy-7-ketocholanic acid (II) obtained by selectively oxidizing cholic acid (I) (in accordance with J.A.C.S. 71, 3935/1949; J.A.C.S. 72, 5530/1950) are dissolved in 2000 ml of secondary butyl alcohol. The solution is raised to boiling, and 100 g of metal sodium are added. Boiling is continued for 2 hours under reflux, and the butyl alcohol is then distilled off while simultaneously feeding an equal quantity of water. When all the butyl alcohol has been removed, the mixture is cooled and acidified with 20% HCl.

The precipitate obtained is filtered, washed with water and dried to give 95 g of a dry amorphous product which on HPLC analysis is found to consist of 88.9% of 3 alpha, 7 beta, 12 alpha-trihydroxycholanic acid, and 9.2% of cholic acid.

Acidimetric titre=99.1%.

$[\alpha]_D^{20} = +71.2°$ (c=1% in dioxane).

200 ml of benzene, 50 ml of pyridine and 50 ml of acetic anhydride are added to 50 grams of 3 alpha, 7 beta, 12 alpha-trihydroxycholanic acid impure with cholic acid, as obtained in the previous stage.

The mixture is allowed to react for 48 hours at 20°–25° C., 50 ml of water are then added under stirring, followed a few minutes later by a mixture of 200 ml of water and 60 ml of 37% HCl. The aqueous phase is discarded and the organic phase is evaporated almost to dryness.

The residue, containing the 3,7-diacetate, is taken up in 500 ml of ethyl acetate, to which 30 ml of 80% acetic acid and 15% sodium hypochlorite are added.

The mixture is left stirring for 1 hour, the excess hypochlorite is destroyed with sodium metabisulphite, and the ethyl acetate is washed with 500 ml of water.

The organic phase is evaporated to dryness, and boiled with 200 ml of 10% of NaOH for 5 hours.

It is acidified with HCl and extracted with ethyl acetate. 45 g of residue are obtained from the organic phase evaporated to dryness, and on HPLC analysis this is found to consist of:

75% of 3 alpha, 7 beta-dihydroxy-12-ketocholanic acid
8% of 3 alpha, 7 alpha-dihydroxy-12-ketocholanic acid
15% of 3 alpha, 7 beta, 12 alpha-trihydroxycholanic acid
2% of cholic acid.

50 grams of impure product obtained from the previous stage are dissolved in 500 ml of N, N-dimethylformamide.

50 g of bis-trimethylsilylurea are added, the mixture is heated to 100° C. and kept under stirring at this temperature for 1 hour, after which it is cooled.

3 alpha, 7 beta-bis-trimethylsilylether-24-trimethylsilyl ester crystallizes out, is filtered off and washed with 50 ml of N, N-dimethylformamide.

It is dried in an oven at 70° C. under vacuum.

60 g of product are obtained having the following characteristics:

M.W.=623.13.
M.P.=155°–157° C.
$[\alpha]_D^{20} = +89°$ (c=2% in dioxane).

50 grams of tris-trimethylsilyl derivative obtained from the previous stage are dissolved in 500 ml of triethylene glycol, 50 ml of 80% hydrazine hydrate and 50 g of KOH are added, and the mixture is heated to about 200° C.

When the reaction has finished, it is cooled, diluted with 2000 ml of water and acidified with HCl.

The product is filtered off, washed with water and crystallized from ethyl acetate.

25 g of ursodeoxycholic acid are obtained having the following characteristics:

M.P.=202°–205° C.
$[\alpha]_D^{20} = +60 \pm 2$ (c=1% in dioxane).
Chenodeoxycholic acid impurity $\leq 1\%$.
Total of other impurities $\leq 0.3\%$.

EXAMPLE 2

100 g of metal potassium are added under boiling conditions to 100 g of 3 alpha, 12 alpha-dihydroxy-7-ketocholanic acid dissolved in 2000 ml of n-butyl alcohol, and the mixture is heated under reflux for 2 hours.

After this time, all the n-butyl alcohol is distilled off while simultaneously feeding water. When distillation has finished, the mixture is acidified with 20% HCl, and the precipitated solid is filtered off.

When the solid (95 g) is subjected to HPLC analysis, it is found to consist of 90% of 3 alpha, 7 beta, 12 alpha-trihydroxycholanic acid, and 10% of cholic acid. The characteristics of the mixture correspond to those of example 1.

1000 g of a mixture of 3 alpha, 7 beta, 12 alpha-trihydroxycholanic acid and cholic acid obtained in the previous stage are dissolved in 150 ml of pyridine, 100 g of succinic anhydride are added, and the mixture is heated to 80° C. for 5 hours.

It is cooled to 0° C. and 100 ml of water added. It is left stirring for 2 hours. 1000 ml of ethyl acetate are added, and the pH adjusted to 3–3.5 with HCl. The aqueous phase is separated.

50 ml of acetic acid and 50 ml of a 10% aqueous solution of KBr are added to the organic solution obtained in the previous stage, and its temperature is then adjusted to 20° C. While maintaining this temperature, 150 ml of a 15% solution of sodium hypochlorite are added.

The mixture is left stirring for 30 minutes, the product is filtered off, washed with 200 ml of ethyl acetate and dried in an oven at 80° C.

The dry product is boiled for 2 hours with 1000 ml of 10% NaOH, it is then cooled, 1000 ml of ethyl acetate are then added, and the mixture acidified with 20% of HCl. The organic phase is separated and evaporated to a volume of about 300 ml.

It is cooled to 0° C. and filtered.

The product is washed with 100 ml of ethyl acetate, and dried in an oven at 80° C.

70 g of impure 3 alpha, 7 beta-dihydroxy-12-ketocholanic acid are obtained.

100 ml of acetonitrile, 700 ml of hexamethyldisilazane and 300 ml of trimethylchlorosilane are added to 100 g of impure 3 alpha, 7 beta-dihydroxy-12-ketocholanic acid as obtained in the previous stage. It is heated under reflux for 1 hour and then cooled.

The 3 alpha, 7 beta-bis-trimethylsilylether-24-trimethylsilylester crystallizes out, is filtered off, washed with acetonitrile and dried at 60° C. under vacuum.

50 g of the tris-trimethylsilyl derivative thus obtained are dissolved under stirring in 500 ml of ethyl acetate and 100 ml of 10% HCl at a temperature of 50° C. for 10 minutes. The organic phase is separated and washed with 100 ml of water. On concentrating, very pure 3 alpha, 7 beta-dihydroxy-12-keto-5 beta-cholanic acid crystallizes out, is filtered, washed with ethyl acetate and dried in an oven at 80° C.

Characteristics:
M.W.=406.5
M.P.=190° C.
$[\alpha]_D^{20} = +108° \pm 3$ (c=1% in dioxane).
Total impurities determined by chromatography $\leq 0.5\%$.

50 g of pure 3 alpha, 7 beta-dihydroxy-12-ketocholanic acid are dissolved in 500 ml of triethylene glycol, 50 ml of 80% hydrazine hydrate and 50 g of KOH, and the solution is heated to 200° C. for 1 hour.

When the reaction is finished, the mixture is cooled, diluted with 200 ml of water and acidified with HCl. The product is separated by filtration and crystallizes from ethyl acetate.

45 g of very pure ursodeoxycholic acid are obtained, having the following characteristics:
M.P.=202°-205° C.
$[\alpha]_D^{20} = +60° \pm 2$ (c=1% in dioxane).
Total impurities $\leq 1\%$.

EXAMPLE 3

The preparation as described in example 1 is repeated exactly, with the exception of the stage involving the preparation of the tris-trimethylsilyl derivative, which is carried out as follows:

50 ml of bis-trimethylsilyl-acetamide are added to 50 g of impure 3 alpha, 7 beta-dihydroxy-12-ketocholanic acid dissolved in 500 ml of N,N-dimethylformamide. The mixture is heated to 100° C., is kept at this temperature for 1 hour under stirring, and is then cooled.

The filtered precipitate is recrystallized from N,N-dimethylformamide in the presence of 10 ml of bis-trimethylsilyl-acetamide at 100° C. for 1 hour. It is filtered off, washed and dried at 70° C. under vacuum.

61 g of the tris-trimethylsilyl derivative of 3 alpha, 7 beta-dihydroxy-12-ketocholanic acid are obtained, having the same characteristics as described in example 1.

We claim:

1. A process for preparing high purity ursodeoxycholic acid

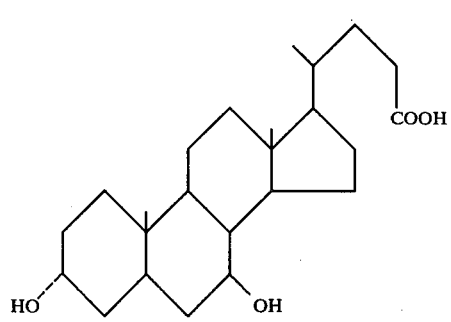

characterised in that a compound of formula

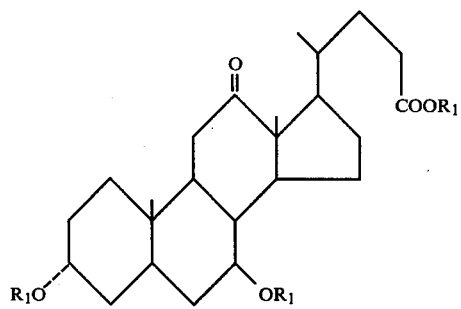

in which $R_1$=H or a —Si(CH$_3$)$_3$ group, is reduced with hydrazine hydrate in the presence of an alkaline base and triethylene glycol, and the product obtained, if $R_1$=—Si(CH$_3$)$_3$ is subjected to acid hydrolysis.

2. A process as claimed in claim 1, characterized in that the compound of formula:

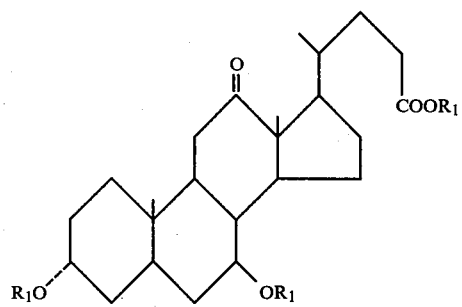

in which $R_1$=Si(CH$_3$)$_3$, is prepared from the corresponding compound in which $R_1$=H by treatment with a silanizing agent in an organic solvent solution.

3. A process as claimed in claim 1, characterized in that the compound of formula

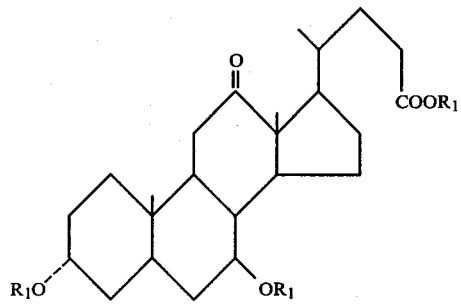

in which $R_1$=H, is prepared from the compound of formula

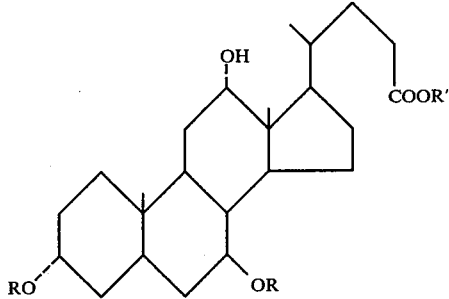

in which R is an aliphatic or aromatic acid radical and R'=H or an alkyl of 1–4 C atoms, by oxidation with alkaline hypochlorite in acetic acid, followed by hydrolysis with dilute strong alkali and subsequent acidification.

4. A process as claimed in claim 3, characterized in that the compound of formula

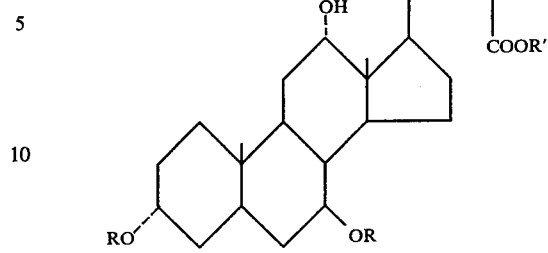

in which R=R'=H, is obtained from the compound of formula by reducing a solution thereof in aliphatic alcohol of 1–4 C atoms, with alkaline metals.